US00PP28930P2

(12) United States Plant Patent
Olesen

(10) Patent No.: US PP28,930 P2
(45) Date of Patent: Feb. 6, 2018

(54) COMPACT FLORIBUNDA ROSE PLANT NAMED 'POULPAL068'

(50) Latin Name: ***Rosa* hybrid**
Varietal Denomination: Poulpal068

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/330,303

(22) Filed: Sep. 6, 2016

(51) Int. Cl.
*A01H 5/08* (2006.01)

(52) U.S. Cl.
USPC ..... Plt./146

(58) Field of Classification Search
USPC ..... Plt./146
See application file for complete search history.

*Primary Examiner* — Annette H Para

(57) ABSTRACT

A new garden rose plant of the compact floribunda class which has abundant, orange blend flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal068'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpal068', originated as a single seedling from the stated cross.

The new variety may be distinguished from its male pollen parent and female seed parent primarily by the following characteristics. The male pollen parent plant has light apricot flowers, while the new plant has orange blend flowers. The female seed parent plant grows to a height of 25 cm while the new variety grows to 60 cm in one season.

The objective of the hybridization of this rose variety was to create a new and distinct variety for garden use with unique qualities, such as:

1. Uniform and abundant orange blend flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal068' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpal068' was selected in the spring of 2008 by the inventor as a single plant from the progeny of the aforementioned hybridization.

Asexual reproduction of 'Poulpal068' by traditional budding and rooted cuttings was first done by Mogens N. Olesen in the nursery in Fredensborg, Denmark in July, 2008. This initial and other subsequent asexual propagations conducted in controlled environments have demonstrated that the characteristics of 'Poulpal068' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal068'.

Specifically illustrated in FIG. 1 are open flowers viewed from the side and above, petals detached, sepals detached, and a flower bud.

Figure 1:
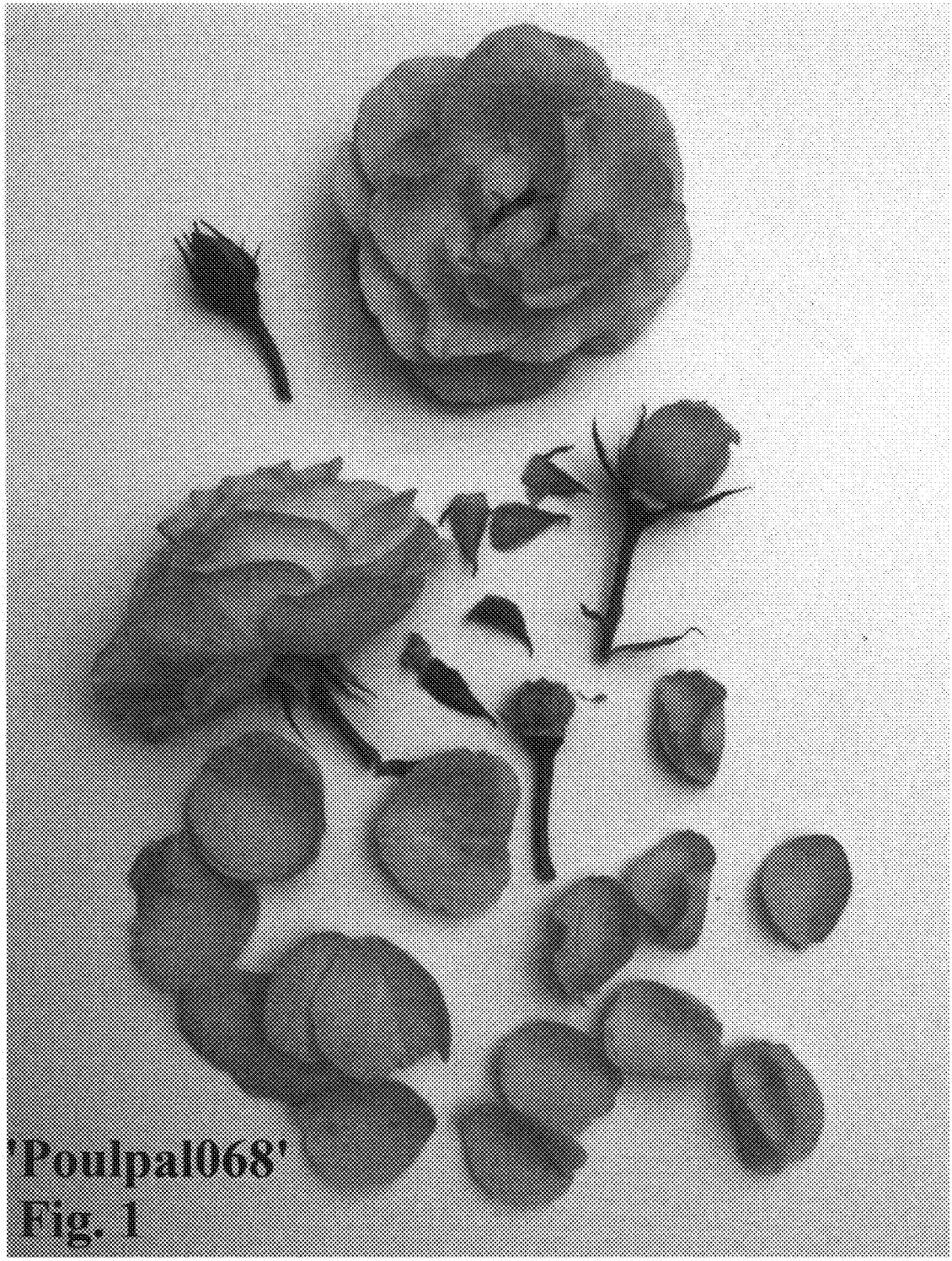
Figure 2:
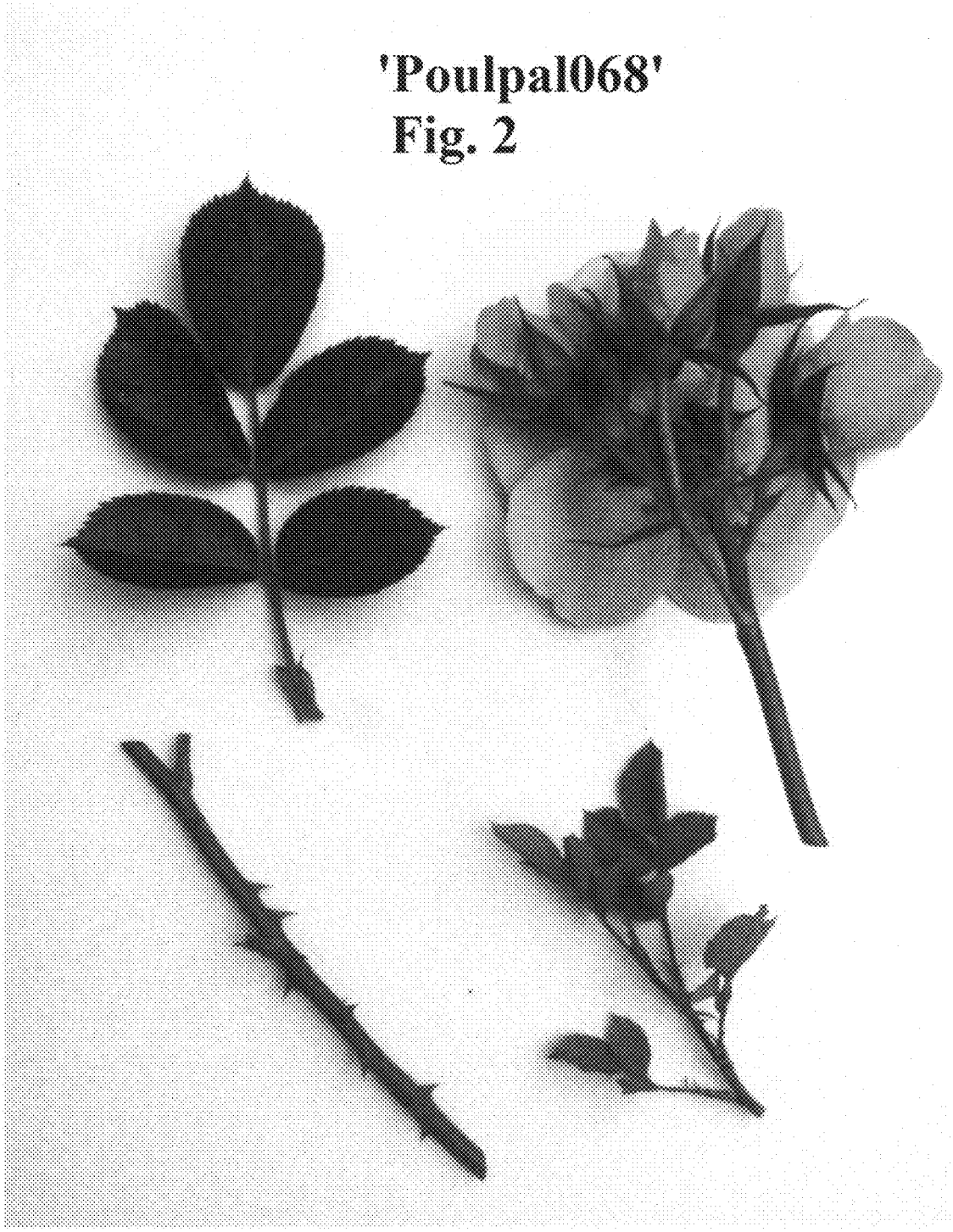

Shown in FIG. 2 are bare stem, mature leaf, juvenile leaves and stems, and a cluster of open flowers. Plants shown are 2 years of age.

DETAILED DESCRIPTION OF THE VARIETY

The following is a description of 'Poulpal068', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulymp', U.S. Plant Pat. No. 16,744 are compared to 'Poulpal068' in Chart 1.

CHART 1

| | 'Poulpal068' | 'Poulymp' |
|---|---|---|
| Petal Count | 25 | 25 to 30 |
| Flower Diameter | 80 mm | 60 to 70 mm |

CHART 1-continued

| | 'Poulpal068' | 'Poulymp' |
|---|---|---|
| General Tonality of Flower Color | Yellow-Orange Group 23C and Orange Group 29A, blended | Yellow-Orange Group 20B, Orange Group 24C, and Yellow-Orange Group 21C |

FLOWER AND FLOWER BUD

Blooming habit: Continuous.

Flower bud:

*Size*.—Upon opening, 18 mm in length from base of receptacle to end of bud. Bud diameter is 5 mm.

*Bud form*.—Ovoid.

*Bud color*.—As sepals divide petals are Orange-Red Group 34A and Orange-Red Group 30B.

*Sepal inner surface*.—Color: Yellow-Green Group 144A. Surface: Lightly pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—19 mm long, 10 mm wide.

*Receptacle*.—Texture: Smooth. Size: 10 mm in height, 10 mm wide. Color: Yellow-Green Group 144A. Shape: Campanulate.

*Pedicel*.—Surface: Smooth. Length: 25 to 30 mm. Diameter: 2 mm on average. Color: Yellow-Green Group 144A. Strength: Strong.

*Peduncle*.—Length: 1 to 3 cm. Diameter: About 4 mm. Color: Yellow-Green Group 145A. Texture: Smooth.

Flower bud development: Flower buds are borne in clusters of about 5 flower buds per stem.

Flower bloom:

*Fragrance*.—Moderate perfume.

*Duration*.—The blooms have a duration on the plant of approximately 10 days. Petals fall cleanly away from plant after flowers have fully matured.

*Size*.—Flower diameter is 80 mm when open. Flower depth is 40 mm.

*Flower shape*.—Partially open cup, semi double flower, with petals that curve out from the center.

*Shape of flower, side view*.—The upper portion is convex. The lower portion is concave.

Petalage: Under normal conditions, flowers have about 25 petals.

General tonality of flower: Open flowers are a blend of Yellow-Orange Group 23C and Orange Group 29A.

Petal color:

*Upon and after opening, outer and inner petals are*.—Upper surface: Yellow-Orange Group 23C with intonations of Orange Group 29A, splashed with Yellow Group 13A. Lower surface: Orange Group 25C splashed with intonations of Yellow Group 13B and Orange Group 29A.

Petals:

*Petal reflex*.—Slightly reflexed.

*Margin*.—Entire and uniform. Moderate undulations.

*Shape*.—Generally rounded and broad. Apex shape: Rounded. Base shape: Rounded.

*Size*.—32 mm (l)×30 mm (w).

*Texture*.—Smooth.

*Thickness*.—Average.

Petaloids: None.

Reproductive flower parts:

*Pollen*.—None observed.

*Anthers*.—Size: 2 mm in length. Color: Yellow Group 4B. Quantity: 40 on average.

*Filaments*.—Color: Yellow-Orange Group 23A. Length: 5 mm.

*Pistils*.—Length: 7 mm. Quantity: 28 on average.

*Stigmas*.—Color: Greyed-Yellow Group 162A.

*Styles*.—Color: Green-White Group 152A.

*Location of stigmas*.—Slightly superior in location relative to the length of the filaments and the height of the anthers.

*Hips*.—None Observed.

PLANT

Plant growth: Upright, bushy. Plants are about 60 cm in height, and 60 cm wide.

Stems:

*Color*.—Juvenile growth: Yellow-Green Group 144A. Mature growth: Yellow-Green Group 144B.

*Length*.—On average, canes are 25 cm from the base of the plant to the flowering portion.

*Diameter*.—6 mm.

*Internodes*.—On mature canes about 30 mm between nodes.

*Surface texture*.—Young wood: Smooth. Older wood: Smooth.

Long prickles:

*Incidence*.—9 prickles per 10 cm of stem.

*Size*.—Average length of prickles on mature stems is 5 mm.

*Shape*.—Upper portion is linear. Lower portion is concave.

*Color*.—Juvenile prickles: Greyed-Red Group 182A. Mature prickles: Greyed-Red Group 182A.

Plant foliage:

*Compound leaf*.—120 mm (l)×80 (w).

*Quantity*.—2 to 3 leaves per 10 cm of stem on average.

*Leaf bearing angle to the stem*.—45 degrees.

*Color of juvenile foliage*.—Upper side: Yellow-Green Group 144A with marginal intonations of Greyed-Red Group 182A. Lower side: Yellow-Green Group 144B.

*Color of mature foliage*.—Upper side: Yellow-Green Group 147A. Lower side: Yellow-Green Group 146B.

Plant leaves and leaflets:

*Stipules*.—Size: 17 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 20 mm. Diameter: 2 mm.

*Upper surface*.—Color: Yellow-Green Group 144A.

*Lower surface*.—Color: Yellow-Green Group 144A.

*Rachis*.—Length: 50 mm. Upper surface: Color: Yellow-Green Group 144A.

*Lower surface*.—Color: Yellow-Green Group 144A.

*Leaflet*.—Quantity: Normally 5 leaflets. Margins: Serrated. Size: On average terminal leaflets are 45 mm long, 32 mm wide. Shape: Generally elliptical. Base: Rounded. Apex: Cuspidate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the compact floribunda rose class named 'Poulpal068', substantially as illustrated and described herein, due to its abundant orange blend flowers, disease resistance, and extended period of bloom.

* * * * *

'Poulpal068'

'Poulpal068'